United States Patent
Kamatani et al.

(10) Patent No.: US 8,268,455 B2
(45) Date of Patent: Sep. 18, 2012

(54) ORGANIC COMPOUND FOR LIGHT-EMITTING DEVICE, LIGHT-EMITTING DEVICE, AND IMAGE DISPLAY APPARATUS

(75) Inventors: Jun Kamatani, Tokyo (JP); Ryota Ooishi, Yokohama (JP); Shinjiro Okada, Kamakura (JP); Takao Takiguchi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1178 days.

(21) Appl. No.: 11/686,030

(22) Filed: Mar. 14, 2007

(65) Prior Publication Data

US 2007/0231600 A1    Oct. 4, 2007

(30) Foreign Application Priority Data

Mar. 31, 2006    (JP) .................. 2006-099893

(51) Int. Cl.
*H01L 51/54* (2006.01)
*C09K 11/06* (2006.01)

(52) U.S. Cl. ........ 428/690; 428/917; 313/504; 313/506; 257/40; 546/10; 548/103

(58) Field of Classification Search .................. 428/690, 428/917, 411.1, 336; 313/502–509; 257/40, 257/88, 104, E51; 548/101, 103
See application file for complete search history.

(56) References Cited

U.S. PATENT DOCUMENTS

| | | | |
|---|---|---|---|
| 7,589,203 B2 | 9/2009 | Stossel et al. | |
| 2002/0064681 A1 | 5/2002 | Takiguchi et al. | |
| 2005/0253135 A1* | 11/2005 | Stossel et al. | 257/40 |
| 2005/0266153 A1* | 12/2005 | Suzuri et al. | 427/66 |
| 2006/0280968 A1 | 12/2006 | Kamatani et al. | |
| 2007/0228940 A1 | 10/2007 | Hashimoto et al. | |
| 2007/0232803 A1 | 10/2007 | Kamatani et al. | |

FOREIGN PATENT DOCUMENTS

| | | |
|---|---|---|
| JP | 2003-146996 A | 5/2003 |
| JP | 2006-507279 A | 3/2006 |

OTHER PUBLICATIONS

Vincett, et al.; "Electical Conduction and Low Voltage Blue Electroluminescence in Vacuum-Deposited Organic Films"; Thin Solid Films; vol. 94, p. 171-183 (1982).
Burroughes, et al.; "Light-Emitting Diodes Based on Conjugated Polymers", Nature, vol. 347, p. 539-541 (1990).
O'Brien, et al.; Improved Energy Transfer in Electophosphorescent Devices, Applied Physics Letters, vol. 74, No. 3, pp. 442-444 (1999).
Baldo, et al.; "Very High-Efficiency Green Organic Light-Emitting Devices Based on Electrophosphorescence", Applied Physics Letters, vol. 75, No. 1, pp. 4-6 (1999).
Chen, et al., "Recent Developments in Molecular Organic Electroluminescent Materials", Macromol. Symp., vol. 125, pp. 1-48 (1997).
Xie, et al.; "Reduction of Self-Quenching . . . Molecules"; *Adv. Mater.* vol. 13, No. 16, pp. 1245-1248 (2001).

* cited by examiner

*Primary Examiner* — Jennifer Chriss
*Assistant Examiner* — J. L. Yang
(74) *Attorney, Agent, or Firm* — Fitzpatrick, Cella, Harper & Scinto

(57) ABSTRACT

A light-emitting device is provided which uses an organic compound to emit light with high luminance and extremely high efficiency. The organic compound is composed of a metal complex having monovalent bidentate ligands. The light-emitting device includes a pair of electrodes which are an anode and a cathode, and plural organic compound layers interposed between the electrodes, in which at least one layer of the organic compound layers contains a metal complex represented by the following structural formula. The light-emitting device is an organic electroluminescent device using the light-emitting device in which the layer including the organic compound is a light-emitting layer.

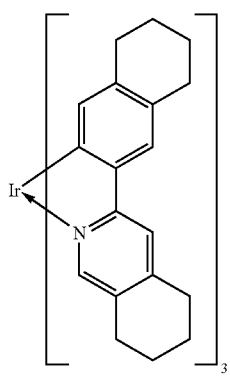
3 Claims, 4 Drawing Sheets

ORGANIC COMPOUND FOR LIGHT-EMITTING DEVICE, LIGHT-EMITTING DEVICE, AND IMAGE DISPLAY APPARATUS

BACKGROUND OF THE INVENTION

1. Field of the Invention

The present invention relates to a novel organic compound for a light-emitting device, a light-emitting device which is used for a plane light source or a flat panel display, and to an image display apparatus.

2. Description of the Related Art

In an old example of an organic light-emitting device, a voltage has been applied to an anthracene evaporated film to emit light (see, Thin Solid Films, 94 (1982), 171). In recent years, applied research has been vigorously conducted on a transformation of an organic light-emitting device into a light-emitting device having high-speed response and high efficiency, including developments of materials for the device. This is because the organic light-emitting device has such advantages that its area can be increased more easily than an inorganic light-emitting device, desired colors can be developed through the developments of various new materials, and it can be operated at a low voltage.

For example, as discussed in Macromol. Symp. 125, 1 to 48 (1997), an organic EL device is generally composed of a transparent substrate, a pair of upper and lower electrodes formed on the transparent substrate, and an organic layer interposed between therebetween including a light-emitting layer.

Recently, investigation has been made into a device utilizing not only conventional light emission utilizing fluorescence ascribable to a transition from an excited singlet state to a ground state but also phosphorescence via a triplet exciton as typified by technologies described in each of "Improved energy transfer in electrophosphoresent device", D. F. O'Brien et al., Applied Physics Letters, Vol 74, No 3, p 422 (1999) and "Very high-efficiency green organic light-emitting devices based on electrophosphorescence", M. A. Baldo et al., Applied Physics Letters, Vol 75, No 1, p 4 (1999). In each of those documents, an organic layer having a four-layer structure has been mainly used. The organic layer includes, from an anode side, a hole-transporting layer, a light-emitting layer, an exciton diffusion-prevention layer, and an electron-transporting layer. Materials used are a carrier-transporting material and a phosphorescent material $Ir(ppy)_3$ shown below.

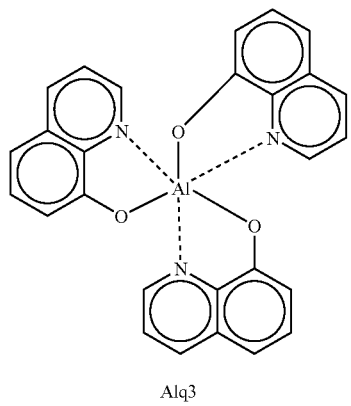

Alq3

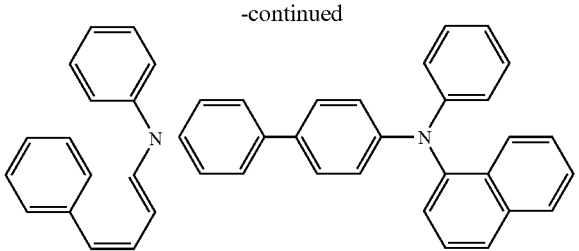

a-NPD

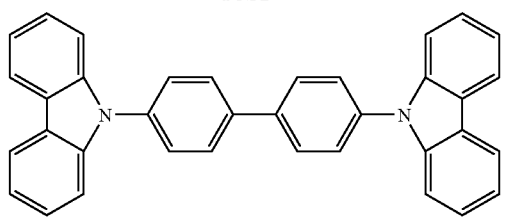

CBP

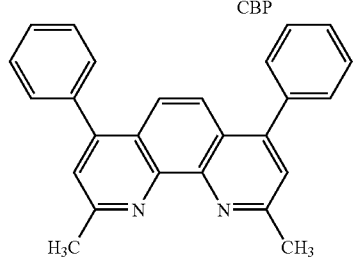

BCP

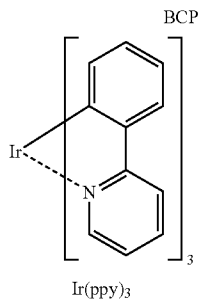

$Ir(ppy)_3$

A variety of light ranging from ultraviolet light to infrared light can be emitted by changing the types of fluorescent organic compounds. In recent years, active research has been conducted on various compounds.

In addition to an organic light-emitting device using any one of the low-molecular-weight materials as described above, an organic light-emitting device using a conjugated polymer has been reported by the group at the University of Cambridge (see, Nature, 347, 539 (1990)). In this report, there has been observed light emission from a single layer by forming polyphenylenevinylene (PPV) into a film by means of a coating system.

As described above, an organic light-emitting device has recently showed significant progress. The organic light-emitting device can be transformed into a high-speed response, thin, and lightweight light-emitting device which can be driven at a low applied voltage and has high luminance and a variety of emission wavelengths, thus suggesting possibilities of a wide variety of applications.

However, under the present conditions, a light output higher in luminance and higher conversion efficiency are being sought. In addition, there still remain a large number of problems in terms of durability such as changes over time during long-term use and deterioration due to an atmospheric gases containing oxygen or moisture.

SUMMARY OF THE INVENTION

The present invention has been made in view of the above-mentioned background art. An object of the present invention is to provide a highly durable light-emitting device which emits light with high efficiency and high luminance for a long period of time, and an organic compound to be used for the light-emitting device. Further, the present invention is aimed at providing a light-emitting device which can easily be produced at a relatively low cost, and an image display apparatus using the light-emitting device of the present invention.

The present invention relates to a metal complex having monovalent bidentate ligands, in which a metal atom is bound with each of moieties in aromatic ring structures of the ligands. The aromatic ring structures each of which is bound with the metal are covalently bound with each other, and each of the aromatic ring structures shares at least 2 carbon atoms with an alicyclic structure in the metal complex. A metal complex having those structures can provide a light-emitting device having high performance in terms of efficiency and durability which have not been achieved in the conventional organic EL device.

According to the present invention, there is provided an organic compound for a light-emitting device (hereinafter, sometimes abbreviated as "organic compound") as described below.

That is, according to one aspect of the present invention, there is provided an organic compound for a light-emitting device, including a metal complex having monovalent ligands each having a partial structure which is represented by the following general formula (1):

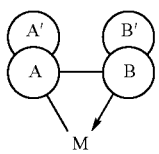

(1)

where A and B each independently represent an aromatic ring structure which may contain a hetero atom(s) which is(are) bound with a metal atom M, and are covalently bound with each other; A' represents a structure including an alicyclic structure whose alicyclic moiety shares at least 2 carbon-carbon bonds with the aromatic ring A, and B' represents a structure including an alicyclic structure whose alicyclic moiety shares at least 2 carbon-carbon bonds with the aromatic ring B, provided that a carbon atom(s) of at least one of the alicyclic structures A' and B' may be replaced by a hetero atom(s); the alicyclic structures may have substituents; when the alicyclic structures have no hetero atoms, the substituents are selected from the group consisting of a hydrogen atom, a halogen atom, a linear or branched alkyl group having 1 to 20 carbon atoms (in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more methylene groups in the alkyl group may be replaced by at least one of an arylene group which may be substituted and a divalent heterocyclic group which may be substituted, and one or two or more hydrogen atoms in the alkyl group may be replaced by a fluorine atom), an amino group which may be substituted, a silyl group which may be substituted, an aryl group which may be substituted, and a heterocyclic group which may be substituted; when the alicyclic structures have hetero atoms, the substituents are selected from the group consisting of a hydrogen atom, a linear or branched alkyl group having 1 to 20 carbon atoms (in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more methylene groups in the alkyl group may be replaced by at least one of an arylene group which may be substituted and a divalent heterocyclic group which may be substituted, and one or two or more hydrogen atoms in the alkyl group may be replaced by a fluorine atom), an amino group which may be substituted, a silyl group which may be substituted, an aryl group which may be substituted, and a heterocyclic group which may be substituted; and M represents a metal atom selected from the group consisting of Ir, Rh, Cu, Zn, Re, Os, and Eu.

It is preferable that the metal complex has in its molecule a central metal of Ir and a skeleton represented by the general formula (1) in the one aspect of the present invention.

In addition, according to another aspect of the present invention, an organic compound for a light-emitting device is provided including a metal complex represented by the general formula (2):

where $L_m$ and $L'_n$ represent bidentate ligands different from each other, m represents an integer of 1 to 3 and n represents an integer of 0 to 2, provided that m+n is 3; and a partial structure $ML_m$ is represented by the general formula (3), and a partial structure $ML'_n$ is represented by any one of the general formulae (4), (5), and (6):

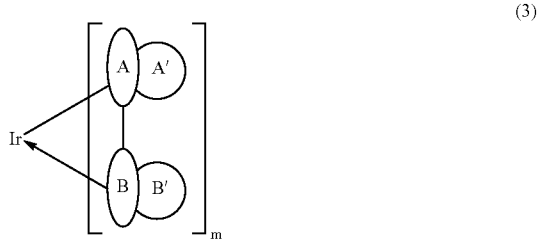

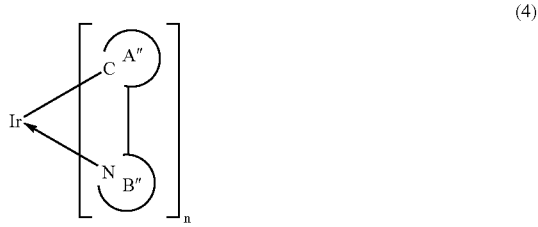

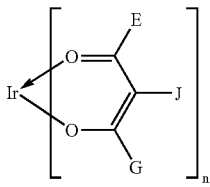

where N represents a nitrogen atom and C represents a carbon atom; A and B each independently represent an aromatic ring structure which may contain a hetero atom(s) which is(are) bound with a metal atom M, and are covalently bound with each other; A' represents a structure containing an alicyclic structure whose alicyclic moiety shares at least 2 carbon-carbon bonds with the aromatic ring A, and B' represents a structure containing an alicyclic structure whose alicyclic moiety shares at least 2 carbon-carbon bonds with the aromatic ring B, provided that a carbon atom(s) of at least one of the alicyclic structures A' and B' may be replaced by a hetero atom(s); the alicyclic structures may have substituents; when the alicyclic structures have no hetero atoms, the substituents are selected from the group consisting of a hydrogen atom, a halogen atom, a linear or branched alkyl group having 1 to 20 carbon atoms (in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more methylene groups in the alkyl may be replaced by at least one of an arylene group which may be substituted and a divalent heterocyclic group which may be substituted, and one or two or more hydrogen atoms in the alkyl group may be replaced by a fluorine atom), an amino group which may be substituted, a silyl group which may be substituted, an aryl group which may be substituted, and a heterocyclic group which may be substituted; when the alicyclic structures have hetero atoms, the substituents are selected from the group consisting of a hydrogen atom, a linear or branched alkyl group having 1 to 20 carbon atoms (in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more methylene groups in the alkyl group may be replaced by at least one of an arylene group which may be substituted and a divalent heterocyclic group which may be substituted, and one or two or more hydrogen atoms in the alkyl group may be replaced by a fluorine atom), an amino group which may be substituted, a silyl group which may be substituted, an aryl group which may be substituted, a pyrenyl group, a phenanthrenyl group, a chrysenyl group, a fluoranthenyl group, a triphenylenyl group, and a heterocyclic group which may be substituted; A" represents a cyclic group which may be substituted and is bound with a metal atom Ir via a carbon atom, and B" represents a cyclic group which may be substituted and is bound with a metal atom M via a nitrogen atom, where A" and B" are covalently bound with each other; E and G are each independently a linear or branched alkyl group having 1 to 20 carbon atoms in which one or two or more hydrogen atoms in the alkyl group may be replaced by a fluorine atom, or an aromatic ring group which may have at least one substituent selected from the group consisting of a halogen atom, a cyano group, a nitro group, a trialkylsilyl group whose alkyl groups are each independently a linear or branched alkyl group having 1 to 8 carbon atoms, and a linear or branched alkyl group having 1 to 20 carbon atoms (in which one or unadjacent two or more methylene groups in the alkyl group may be replaced by at least one group consisting of —O—, —S—, —CO—, —CO—O—, —O—CO—, —CH=CH— and —C≡C—, and one or two or more hydrogen atoms in the alkyl group may be replaced by a fluorine atom); and J represents any one of a hydrogen atom, a halogen atom, a linear or branched alkyl group having 1 to 20 carbon atoms in which one or two or more hydrogen atoms in the alkyl group may be replaced by a fluorine atom, and an aromatic ring group which may have at least one substituent selected from the group consisting of a halogen atom, a cyano group, a nitro group, a trialkylsilyl group whose alkyl groups are each independently a linear or branched alkyl group having 1 to 8 carbon atoms, a linear or branched alkyl group having 1 to 20 carbon atoms (in which one or unadjacent two or more methylene groups in the alkyl group may be replaced by at least one group selected from the group consisting of —O—, —S—, —CO—, —CO—O—, —O—CO—, —CH=CH— and —C≡C—, and one or two or more hydrogen atoms in the alkyl group may be replaced by a fluorine atom).

Specific examples of the aromatic ring structures represented by A and B include a phenyl group, a naphthyl group, a fluorenyl group, an anthracenyl group, a fluoranthenyl group, a pyrenyl group, a thienyl group, a piridyl group, an imidazoyl group, an oxazoyl group, a quinolyl group, an isoquinolyl group, a pyrazyl group, and triazoyl group.

Specific examples of the alicyclic structures represented by A' and B' include a cyclohexyl group, a cyclopentanyl group, and a norbornyl group.

In addition, according to the present invention, in a light-emitting device including a plurality of organic compound layers, at least one layer of the organic compound layers contains at least one of the above-mentioned organic compounds.

The organic compound layer is preferably a light-emitting layer.

The light-emitting layer preferably contains a plurality of phosphorescent materials.

The light-emitting layer preferably includes at least one of the above-mentioned organic compounds.

The organic compound layer is preferably a hole-transporting layer.

The organic compound layer is preferably an electron-transporting layer.

In addition, according to the present invention, there is provided an image display apparatus including the light-emitting device and a unit for supplying an electric signal to the light-emitting device.

The organic compound of the present invention for a light-emitting device is a highly efficient phosphorescent material suitable for emitting blue to red light.

The light-emitting device using the organic compound of the present invention, in particular, an organic light-emitting device using the organic compound as a light-emitting material for a light-emitting layer generates light having high luminance with high efficiency, has high durability, and can be produced easily at a relatively low cost.

It should be noted that the light-emitting device of the present invention includes an organic light-emitting device (also referred to as "organic electroluminescent device" or "organic EL device").

The present invention can provide a light-emitting device which can generate luminescence with high efficiency, can maintain high luminance for a long-term and has high durability, and organic compounds to be used for the light-emitting device. Further, the present invention can provide a light-emitting device which can be produced easily at a relatively low cost. In addition, the present invention can provide an image display apparatus using the light-emitting device of the present invention.

Further features of the present invention will become apparent from the following description of exemplary embodiments with reference to the attached drawings.

DESCRIPTION OF THE EMBODIMENTS

Hereinafter, the present invention will be described in detail.

Figure 1:
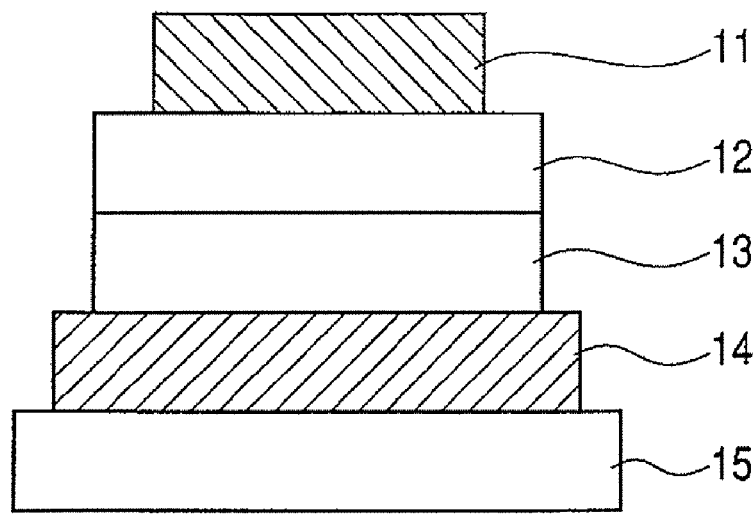
FIG. 1 shows an example of the organic EL device of the present invention.
Figure 2:
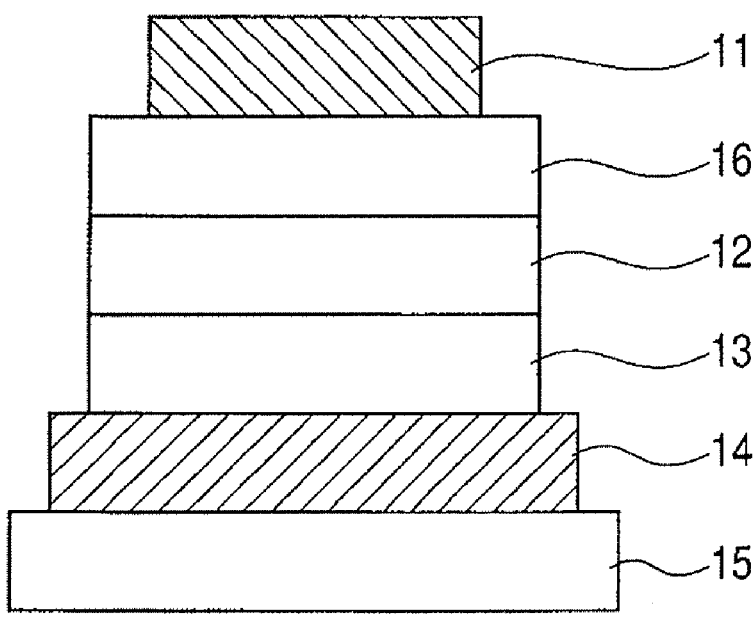
FIG. 2 shows another example of the organic EL device of the present invention.
Figure 3:
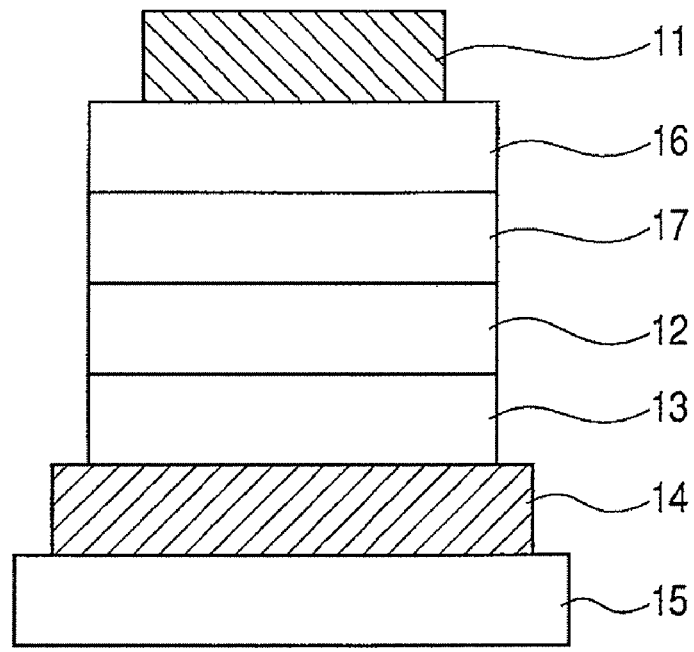
FIG. 3 shows another example of the organic EL device of the present invention.

FIGS. 1, 2 and 3 show basic device structures of the light-emitting device of the present invention.

First, reference characters in the drawings are explained as follows: 11 denotes a metal electrode; 12, a light-emitting layer; 13, a hole-transporting layer; 14, a transparent electrode; 15, a transparent substrate; 16, an electron-transporting layer; 17, an exciton diffusion-prevention layer; 18, a metal electrode layer; and 19, a metal electrode layer.

As shown in FIG. 1, an organic EL device generally includes, on a transparent substrate 15, a transparent electrode 14 having a thickness of 50 to 200 nm, an organic film layer composed of plural layers, and a metal electrode 11 facing the transparent electrode through the organic film layer. The transparent electrode 14 and the metal electrode 11 serve as a pair of electrodes.

FIG. 1 shows an example in which the organic layers include a light-emitting layer 12 and a hole-transporting layer 13. ITO having a large work function is used for the transparent electrode 14 to facilitate the hole injection from the transparent electrode 14 into the hole-transporting layer 13. A metal material having a small work function such as aluminum, magnesium or an alloy thereof is used for the metal electrode 11 to facilitate the electron injection into the organic layers.

The organic compound of the present invention is used for the light-emitting layer 12. A material having electron-donating properties such as a triphenyl diamine derivative typified by α-NPD represented by the following structural formula can also be appropriately used for the hole-transporting layer 13.

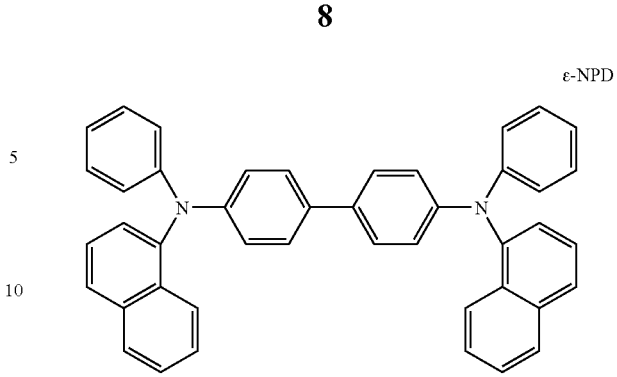

The device having the above-mentioned constitution exhibits electrical rectifying properties. When an electric field is applied in such a manner that the metal electrode 11 serves as a cathode and the transparent electrode 14 serves as an anode, electrons are injected from the metal electrode 11 to the light-emitting layer 12 and holes are injected from the transparent electrode 14.

The injected holes and electrons are recombined in the light-emitting layer 12 to generate excitons, thereby emitting light. In this case, the hole-transporting layer 13 serves as an electron-blocking layer, and the recombination efficiency at the interface between the light-emitting layer 12 and the hole-transporting layer 13 increases, whereby the light emission efficiency increases.

In FIG. 2, an electron-transporting layer 16 is interposed between the metal electrode 11 and the light-emitting layer 12 in FIG. 1. In this case, emission efficiency is increased by separating a light emitting function from electron- and hole-transporting functions to provide a carrier blocking structure having improved effectiveness. An oxadiazole derivative can be used for the electron-transporting layer 16.

As shown in FIG. 3, it is also preferable to employ a four-layer structure composed of, from the side of the transparent electrode 14 as an anode, the hole-transporting layer 13, the light-emitting layer 12, an exciton diffusion-prevention layer 17, the electron-transporting layer 16, and the metal electrode 11.

The organic compound of the present invention is a metal complex having monovalent bidentate ligands, in which a metal atom is bound with each of moieties in aromatic ring structures of the ligands. The aromatic ring structures are covalently bound with each other, and each of the aromatic ring structures shares at least 2 carbon atoms with an alicyclic structure in the metal complex. In this skeleton, an aromatic ring structure present for each conformation is directly bound with an alicyclic structure, whereby concentration quenching among molecules is suppressed, thus the organic compound having the skeleton can be used in a light-emitting layer in a high concentration, even 100%. There is an example of an organic compound in which one of two aromatic ring structures is bound with an alicyclic structure (see, Adv. Mater. 2001, 13, No. 16, August 16). However, in this case, it is difficult to completely suppress the overlapping of aromatic rings among molecules. Further, it is possible to realize transfer and recombination of charges in a molecule by allowing an alicyclic structure to have an aromatic ring structure without conjugation with a ligand so that a complex has a charge-transporting portion. In addition, it is possible to control emission wavelengths by replacing a carbon atom in an alicyclic portion with a hetero atom. Further, it is possible to form a light-emitting layer by incorporating a portion having the skeleton into a polymer.

The light-emitting device having high efficiency of the present invention can be applied to products which require energy saving or high luminance. Examples of applications include a light source for a display apparatus, an illumination apparatus and a printer, and a backlight for a liquid crystal display apparatus. The application of the light-emitting device of the present invention to a display apparatus can provide a lightweight and energy-saving flat panel display with a high level of visibility. In addition, as the light source for a printer, a laser light source for a laser beam printer which is widely used at present can be replaced by the light-emitting device of the present invention. In this respect, independently addressable devices are arranged in an array, and a photosensitive drum is exposed to light in a desired manner to form images. The use of the light-emitting device of the present invention can significantly reduce the volume of an apparatus. The light-emitting device of the present invention is expected to provide an energy-saving effect on the illumination apparatus or the backlight.

The light-emitting device of the present invention may be applied to a display in such a manner that the light-emitting device is driven using an active-matrix TFT drive circuit.

An example of the light-emitting device of the present invention in which an active-matrix substrate is used will be described below with reference to FIGS. 4, 5 and 6.

Figure 4:
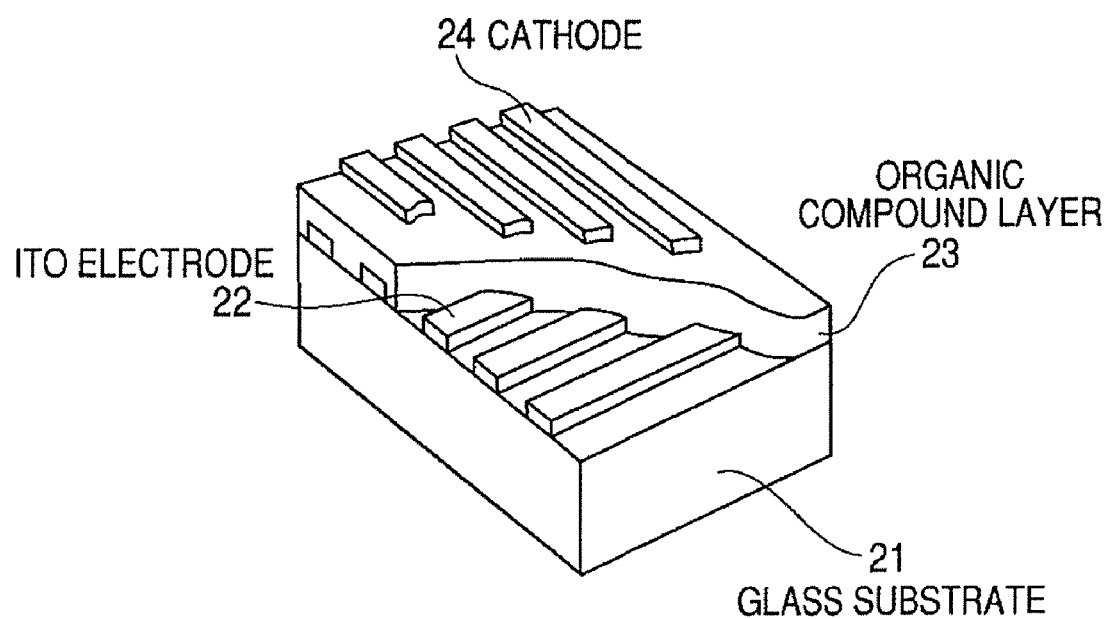
FIG. 4 is a schematical view of a passive type of organic EL device.
Figure 5:
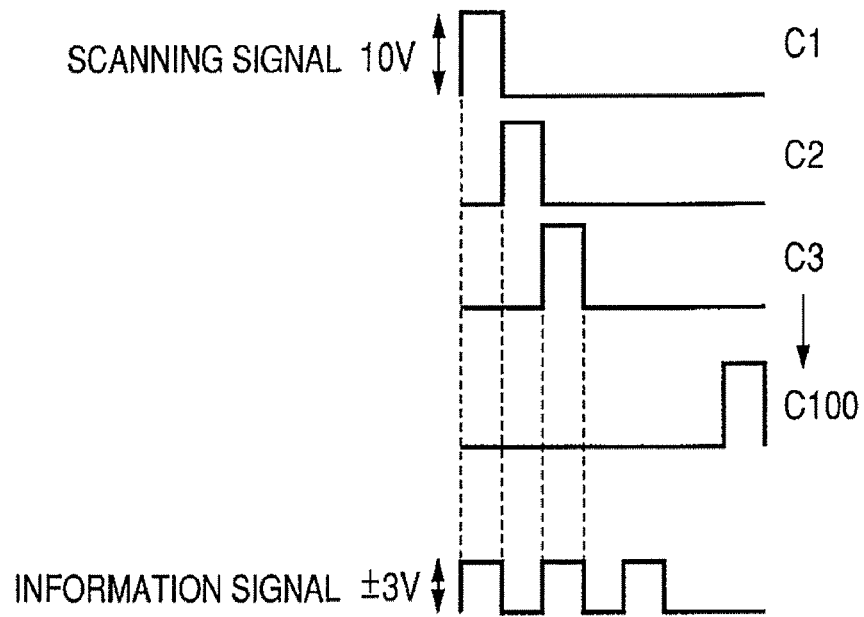
FIG. 5 shows a pixel circuit of a panel.

FIG. 4 schematically illustrates an example of a passive type of organic EL device. In FIG. 4, 21 denotes a glass substrate; 22, an ITO electrode; 23, an organic compound layer; and 24, a cathode. The panel is equipped with a scanning signal driver, an information signal driver, and a current supply source, which are connected respectively to gate selection lines, information signal lines, and current supply lines. A pixel circuit shown in FIG. 5 is placed at the intersection point between the gate selection line and the information signal line. The scanning signal driver sequentially selects the gate selection lines G1, G2, G3, . . . , Gn, and in synchronization therewith, image signals are applied to the gate selection lines from the information signal driver.

Next, the operation of the pixel circuit will be described. In the pixel circuit, when a selected signal is applied to the gate selection line, TFT 1 is turned on to supply an image signal to Cadd so that a gate potential of TFT 2 is determined. Electric current is supplied to the EL device from the current supply line according to the gate potential of TFT 2. Since the gate potential of TFT 2 is retained in Cadd until TFT 1 is again scanned and selected, the gate potential of TFT 2 continues to flow in the EL device until the next scanning is performed. Thus, it is possible to emit light constantly during a one frame period of time.

Figure 6:
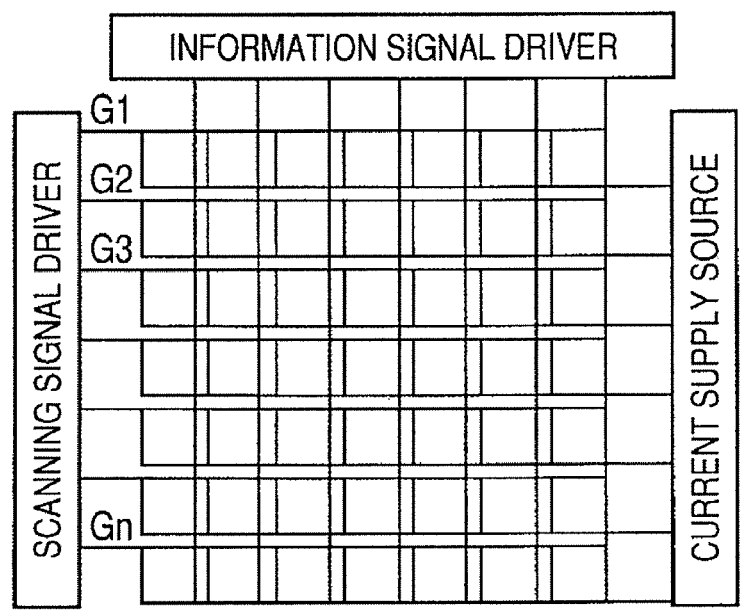
FIG. 6 is a schematic view illustrating an example of a TFT substrate to be used in the present invention.

FIG. 6 schematically illustrates an example of a TFT substrate to be used in the present invention. A p-Si layer is formed on a glass substrate, and necessary impurities are doped in channel, drain and source regions, respectively. A gate electrode is formed thereon through a gate-insulating film, and a drain electrode and a source electrode are so formed as to be connected to the drain region and the source region. On the electrodes, an insulating layer and an ITO electrode as a pixel electrode are superposed, and the ITO electrode and the drain electrode are connected through a contact hole.

In the present invention, a switching device is not particularly limited, and any one of a single-crystal silicon substrate, an MIM device and an a-Si type device can easily be adopted.

An organic EL display panel can be obtained by sequentially superposing a multi-layered or single-layered organic EL layer/cathode layer on the ITO electrode. The display panel using the organic compound of the present invention can be driven to constantly display images with good image quality for a long period of time.

Specific structural formulae of organic compounds used in the present invention are shown below.

However, those formulae are intended merely for showing representative examples, and the present invention is not limited thereto.

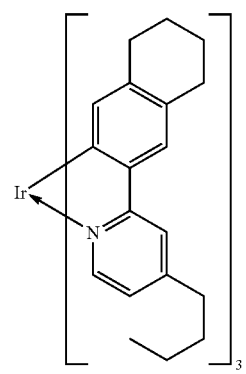

A1

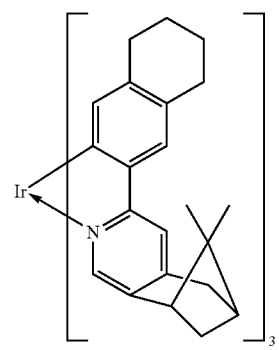

A2

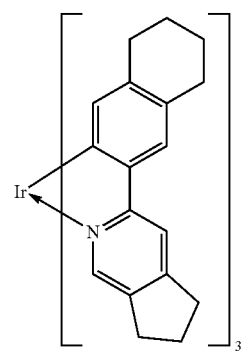

A3

A4 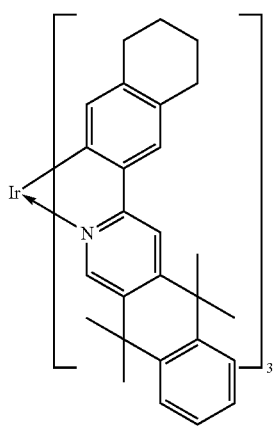
A5 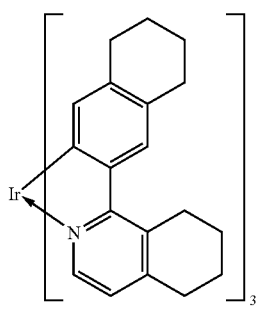
A6 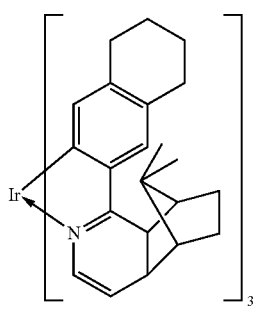
A7 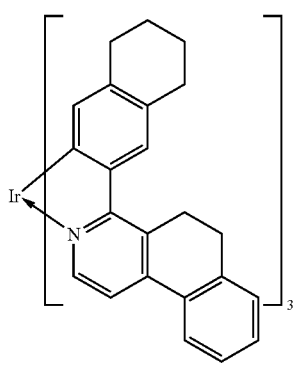
A8 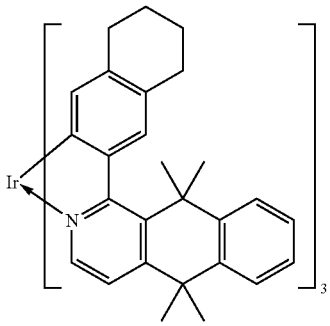
A9 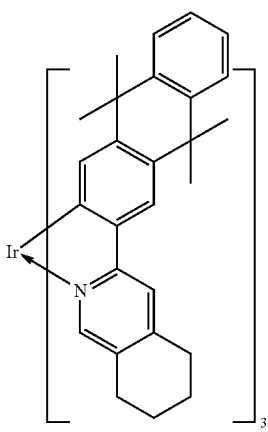
A10 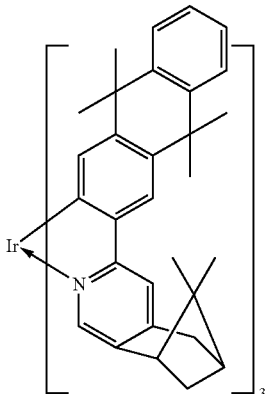
A11 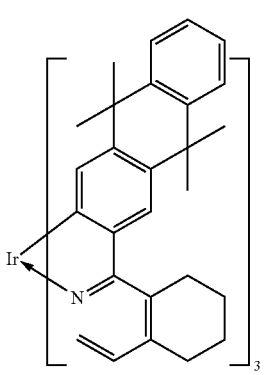

A12
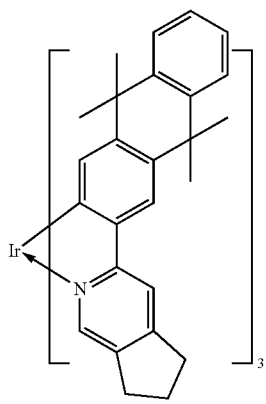
A13
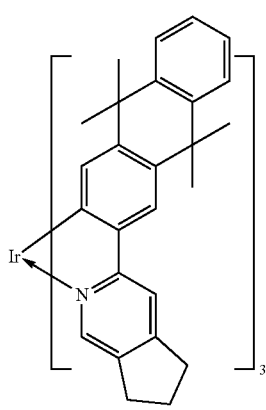
A14
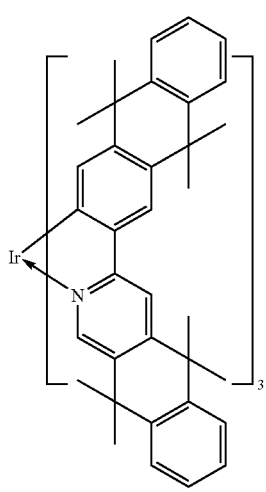
A15
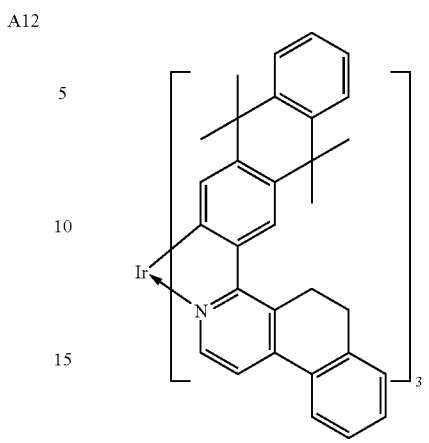
A16
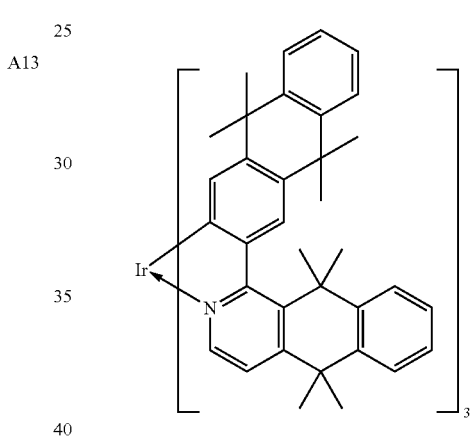
A17
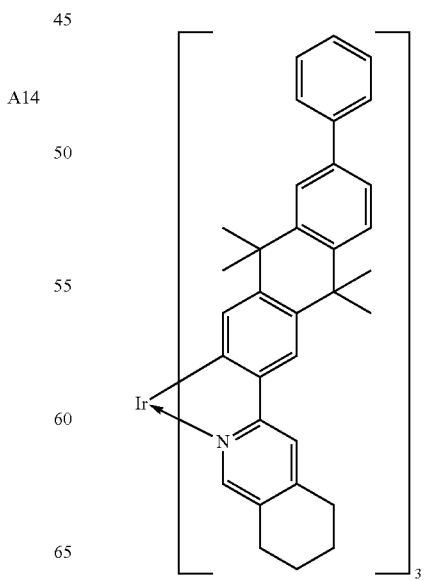

A18
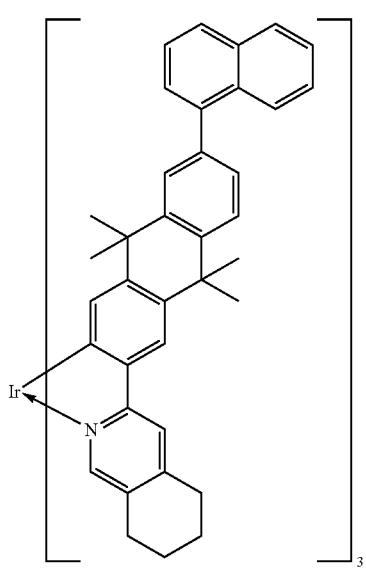
A19
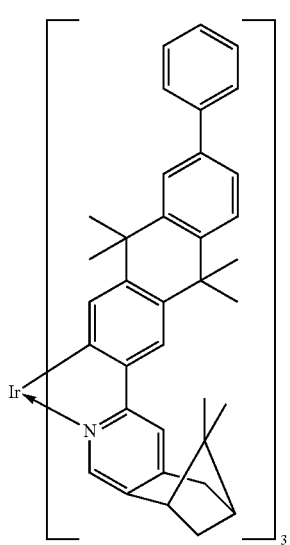
A20
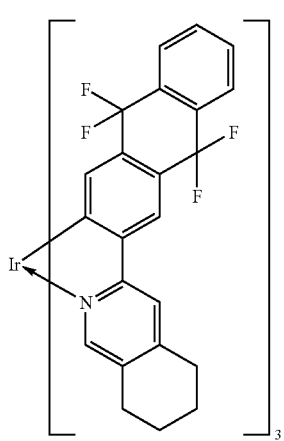
A21
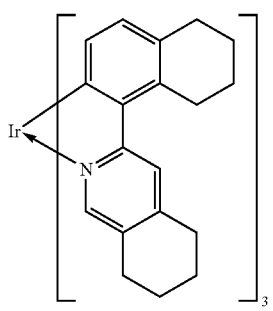
A22
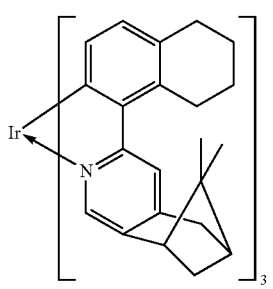
A23
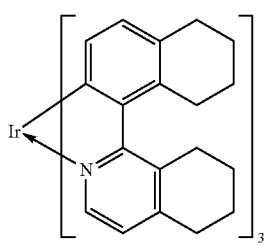
A24
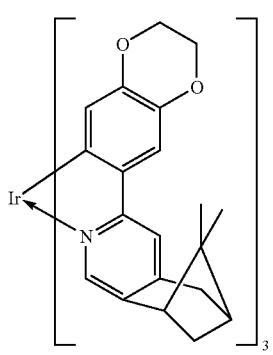
A25
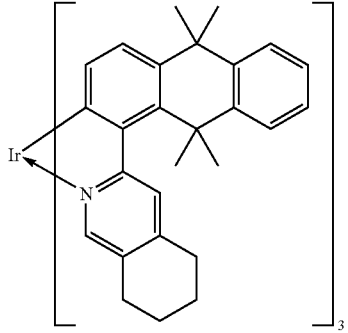

A26
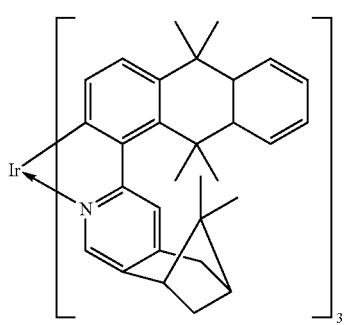
A27
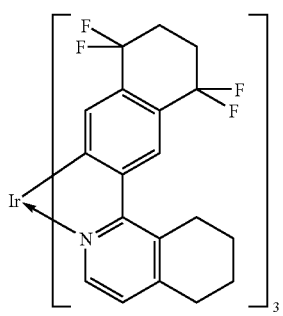
A28
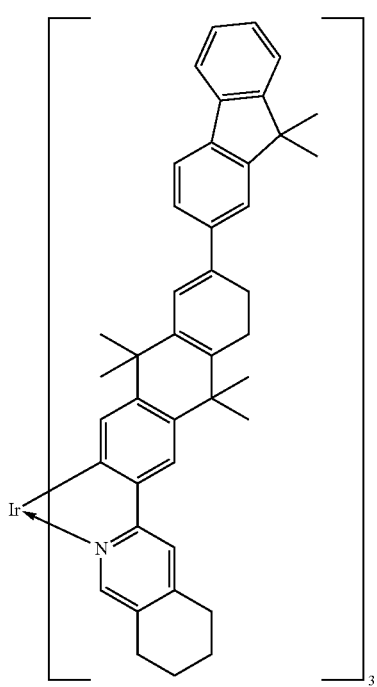
A29
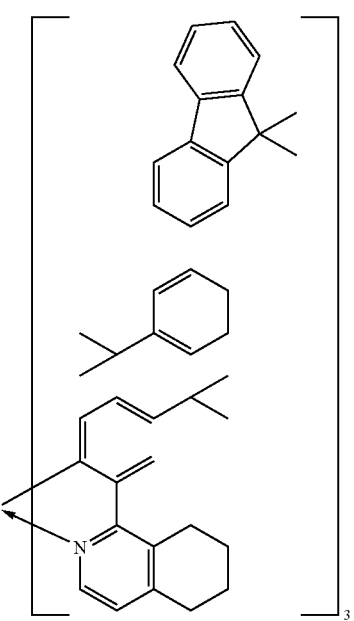
A30
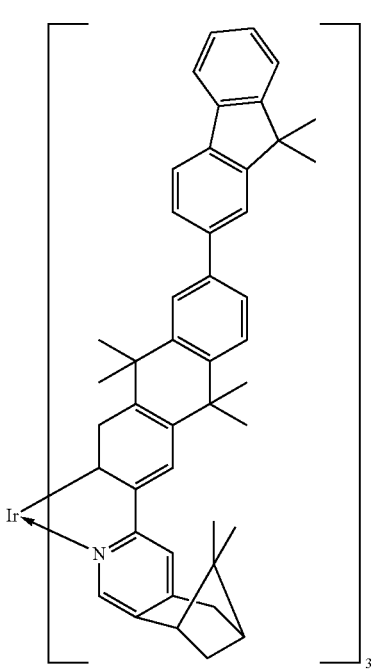

-continued
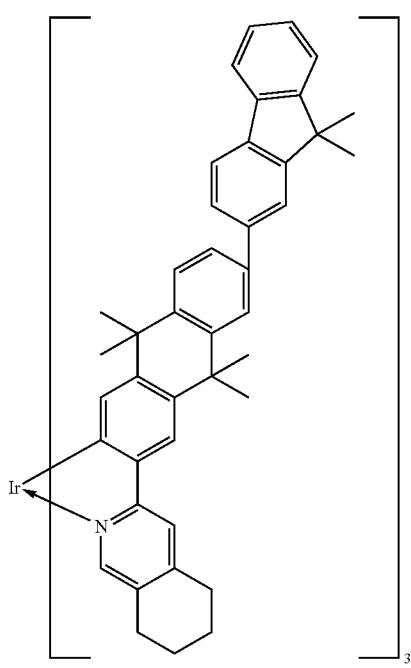
A31
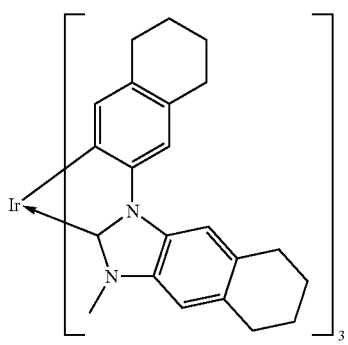
A32
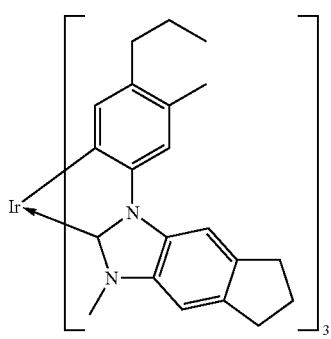
A33
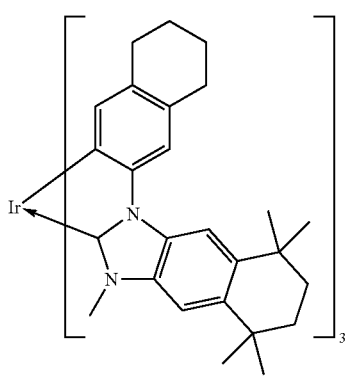
A34
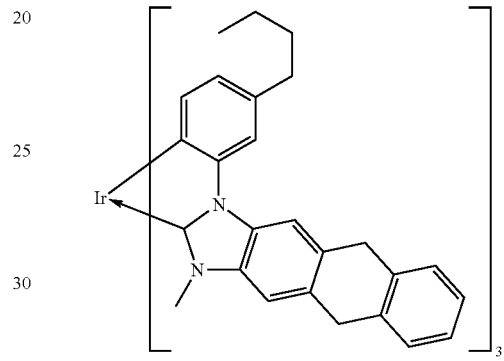
A35
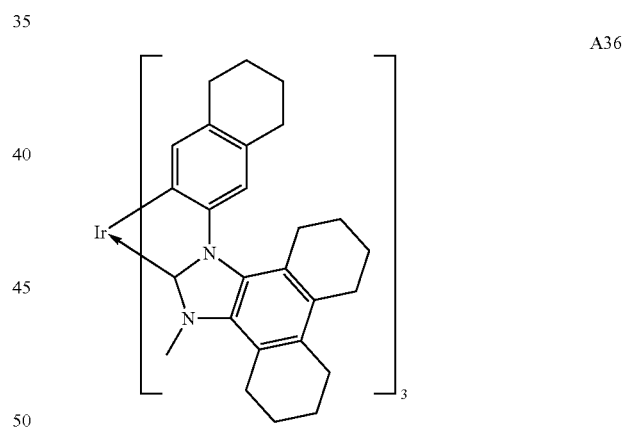
A36
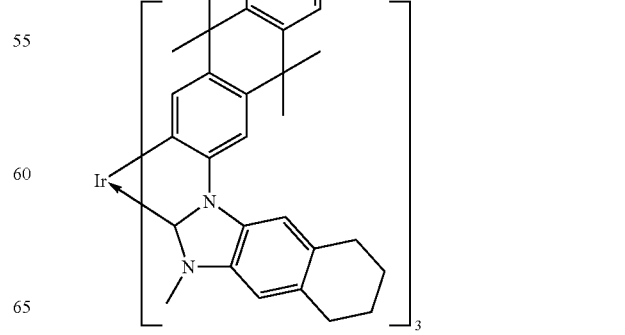
A37

-continued
A38
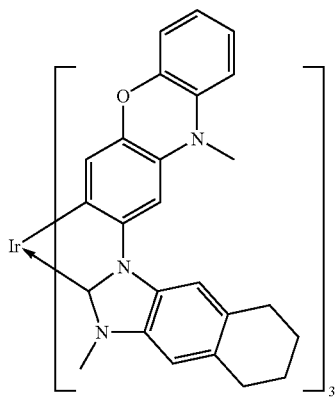
A39
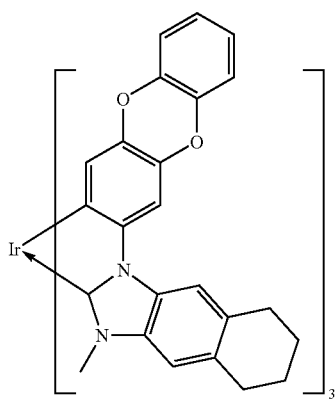
A40
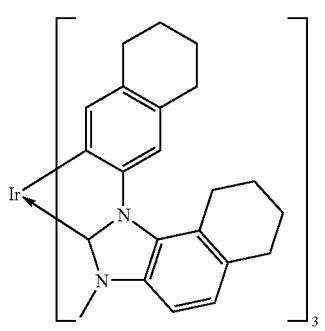
A41
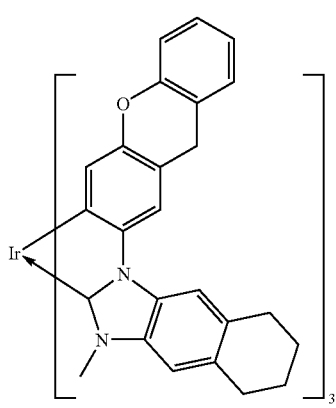
-continued
A42
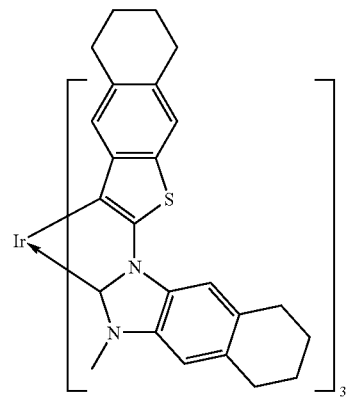
A43
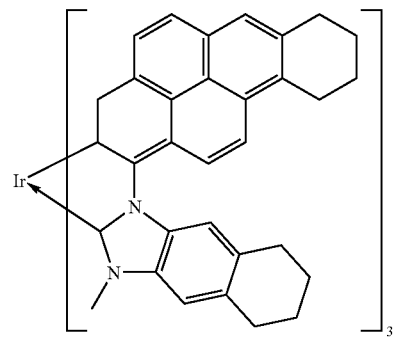
A44
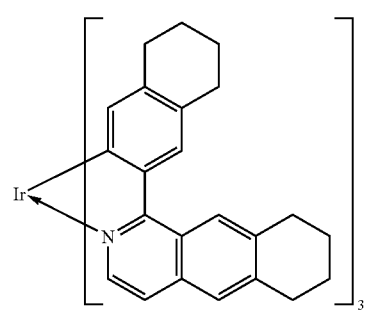
A45
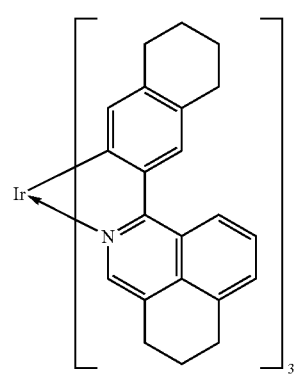
A46
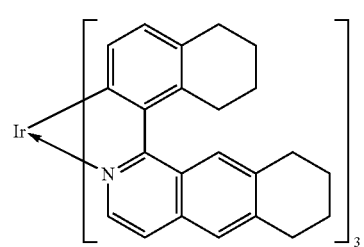

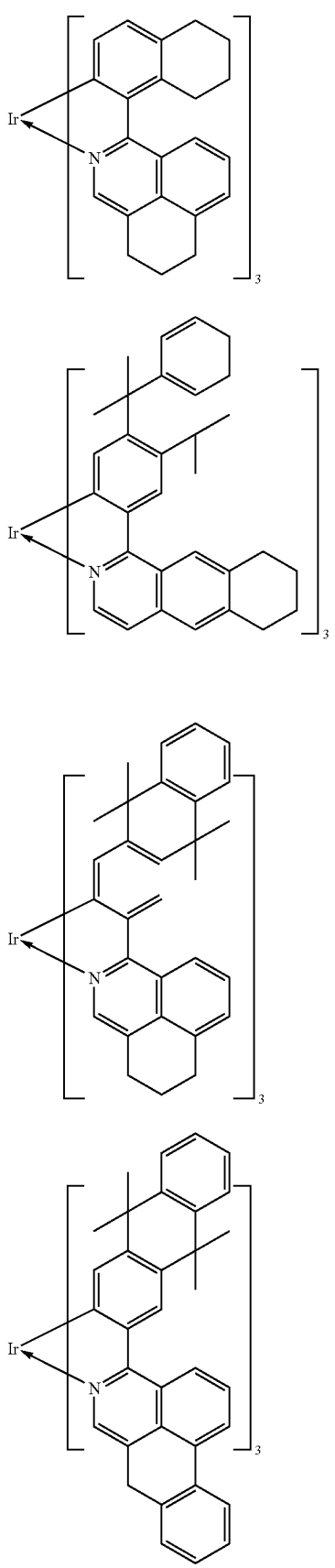
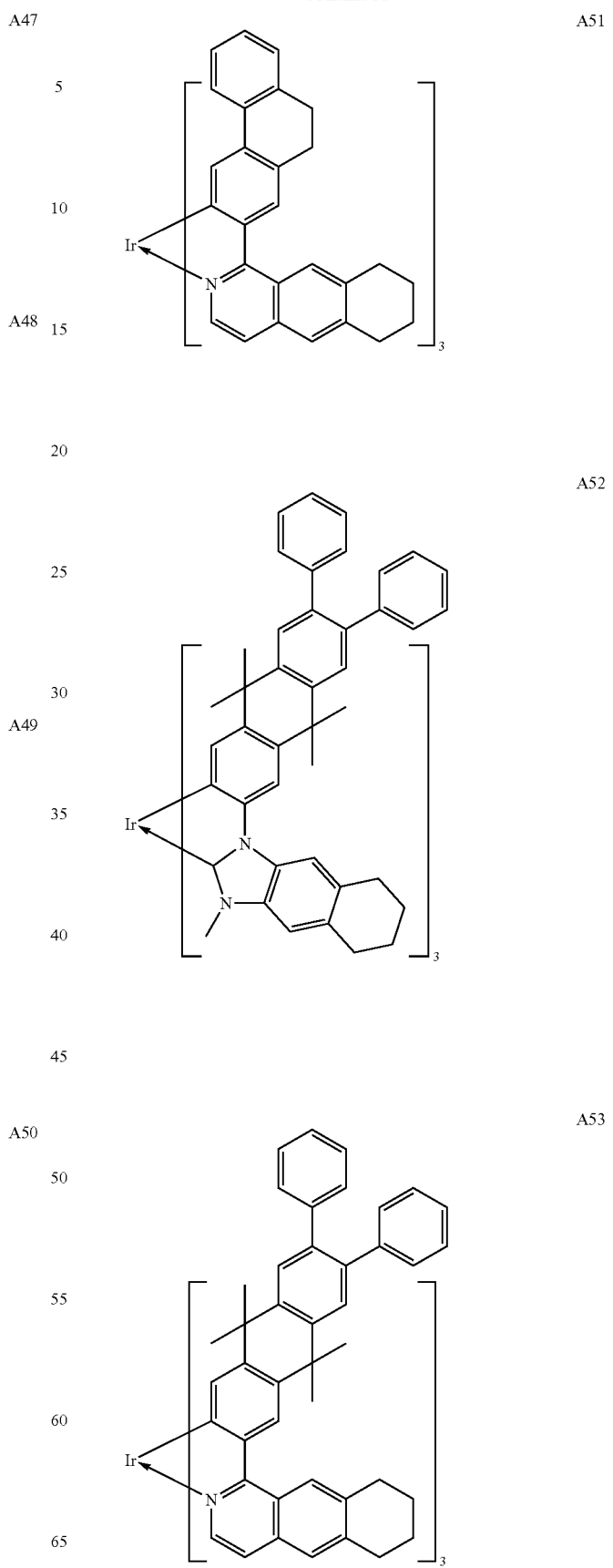

-continued
A54
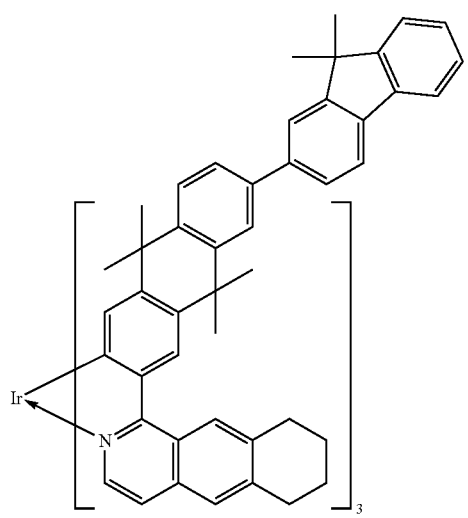
A55
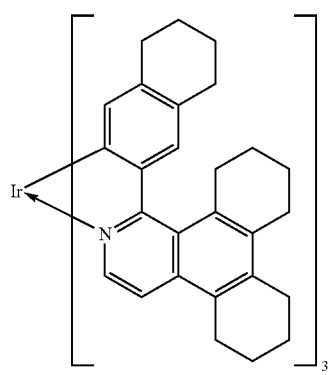
A56
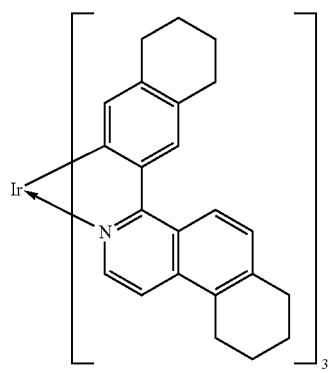
-continued
A57
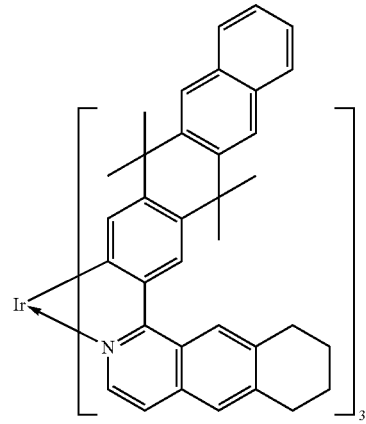
A58
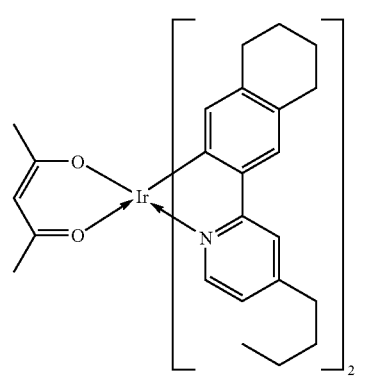
A59
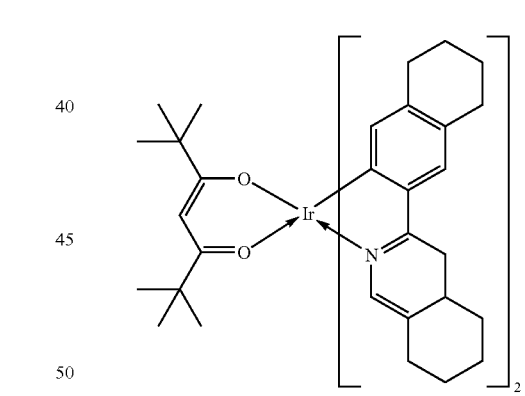
A60
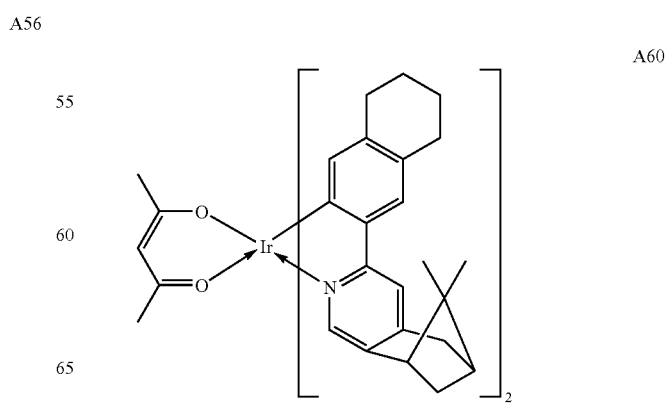

-continued
A61
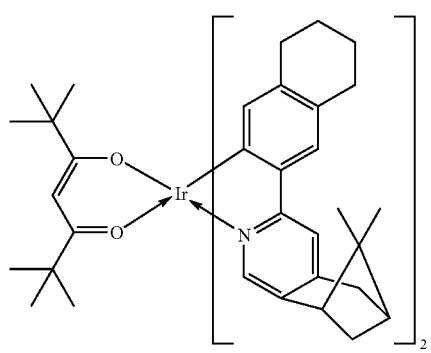
A62
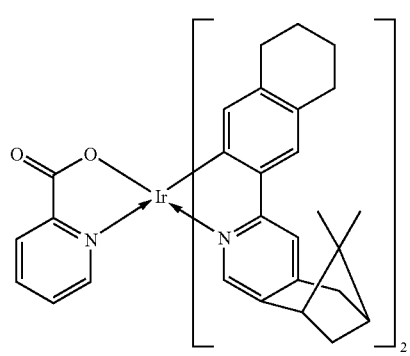
A63
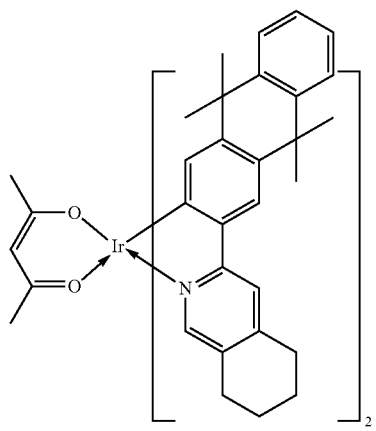
A64
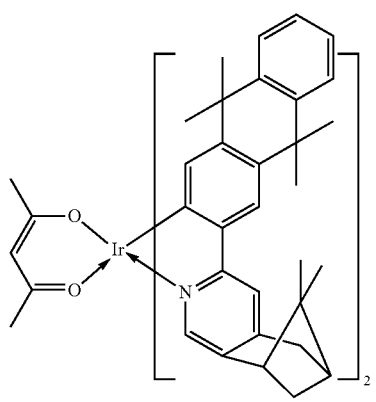
-continued
A65
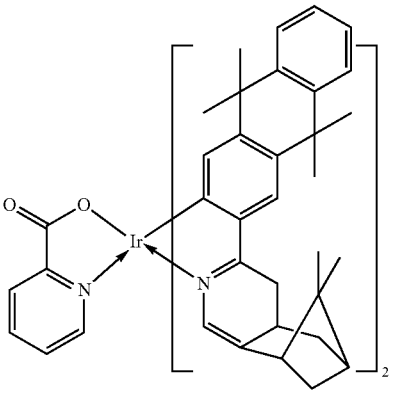
A66
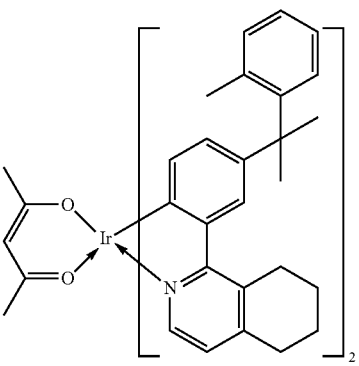
A67
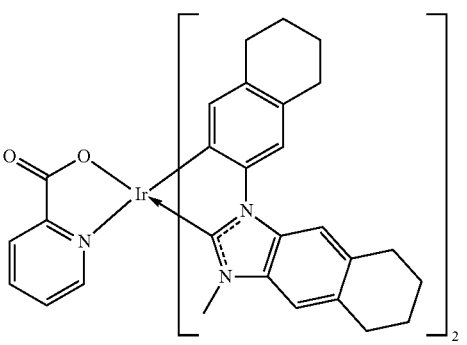
A68
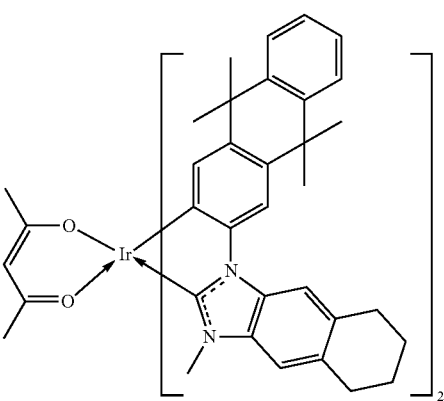

A69
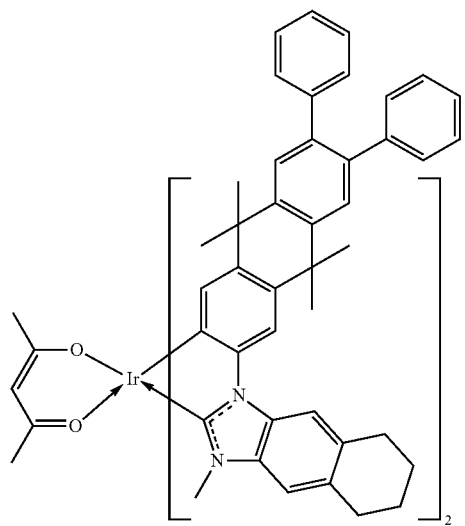
A70
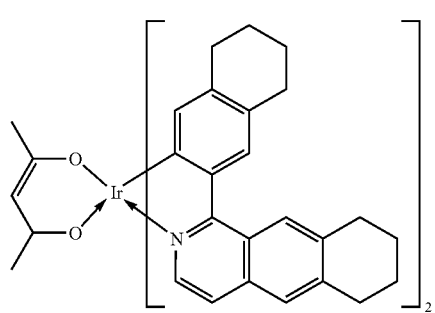
A71
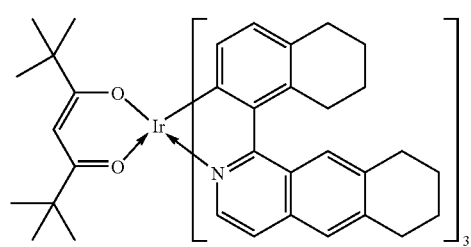
A72
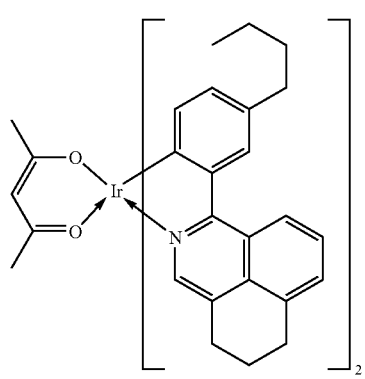
A73
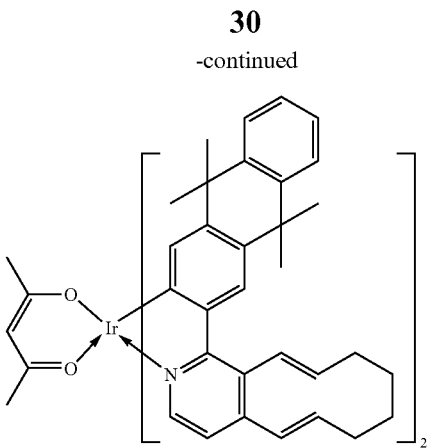
A74
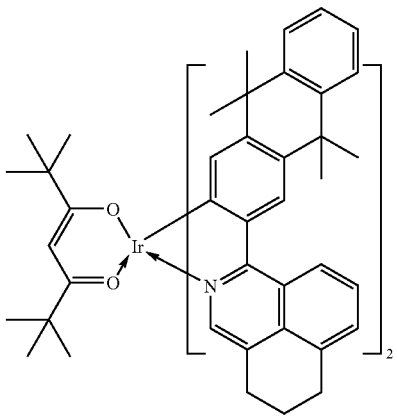
A75
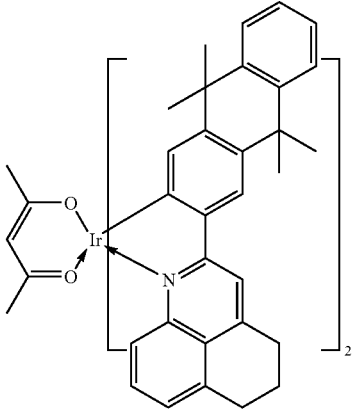
A76
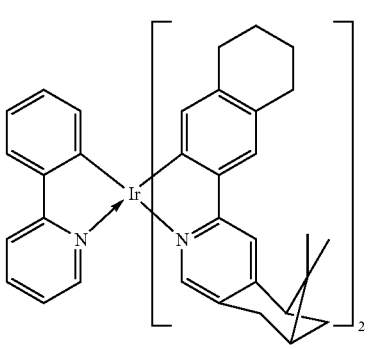

A77
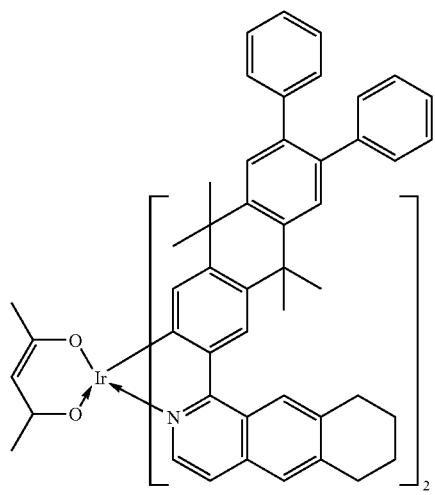
A78
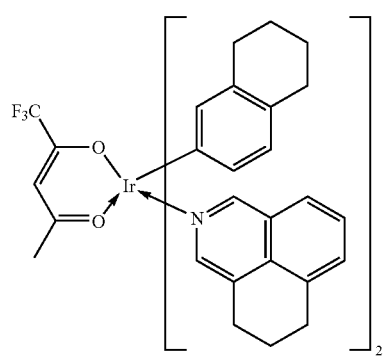
A79
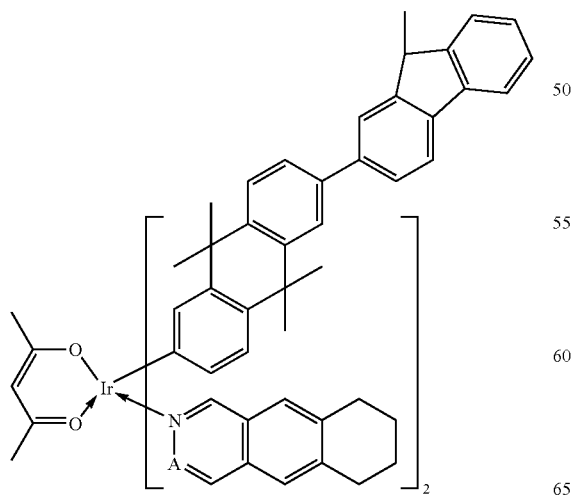
A80
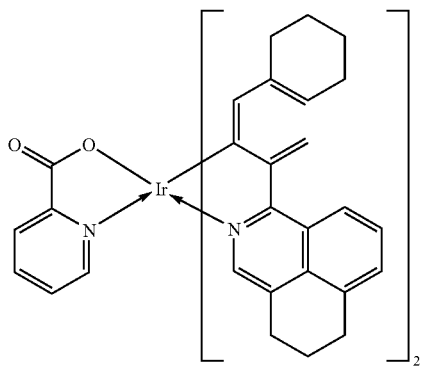
A81
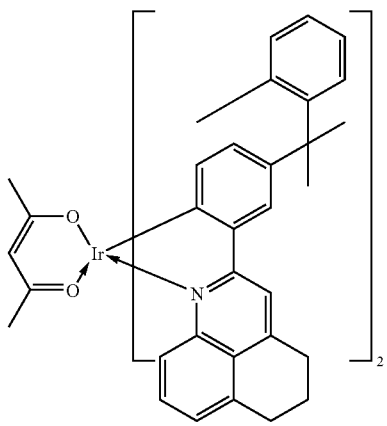
A82
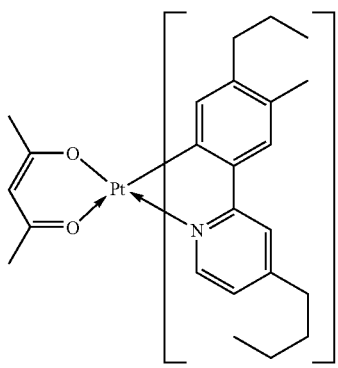
A83
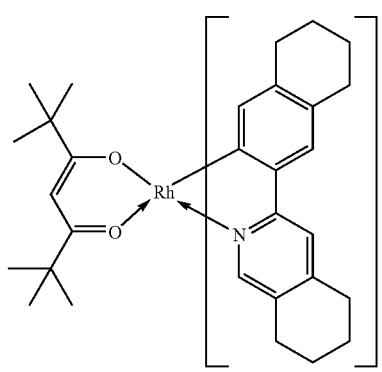

A84
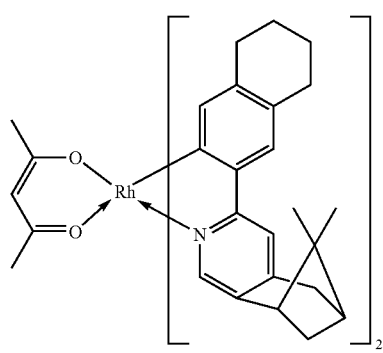
A85
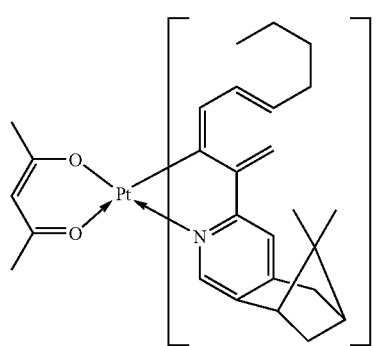
A86
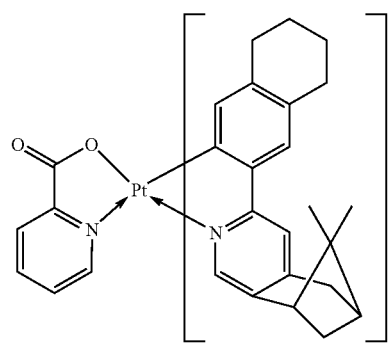
A87
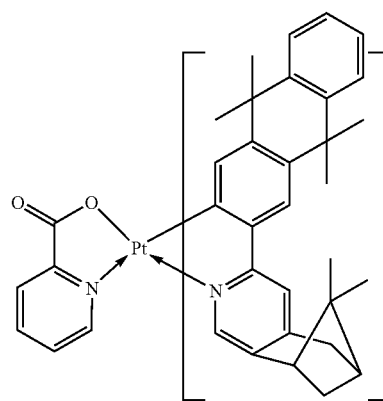
A88
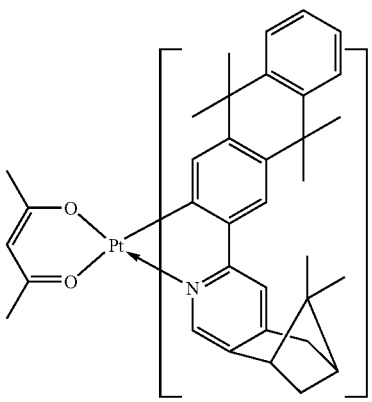
A89
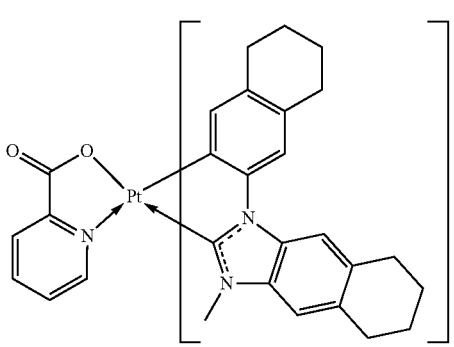
A90
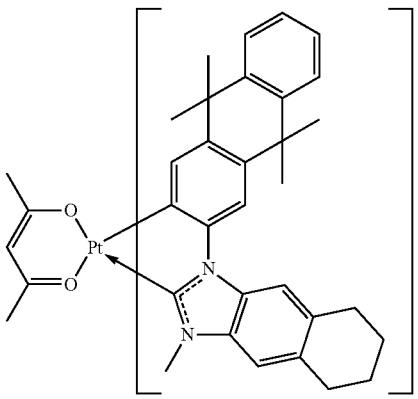
A91
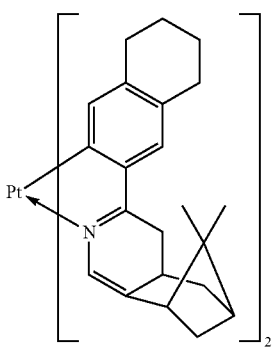

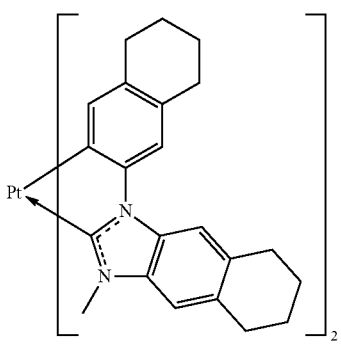

A92

In addition, when the organic compound of the present invention is used for an organic compound layer such as a light-emitting layer of a light-emitting device, the organic compound layer such as a light-emitting layer contains the organic compound of the present invention in a content of 5% by weight or more, preferably 10% by weight or more and 100% by weight or less, and more preferably 51% by weight or more and 100% by weight or less.

EXAMPLES

Hereinafter, the present invention will be described specifically by way of examples. However, the present invention is not limited to these examples.

Representative synthesis examples concerning synthesis methods necessary for synthesizing exemplified compounds are shown below.

Example 1

Synthesis of Exemplified Compound No. A60

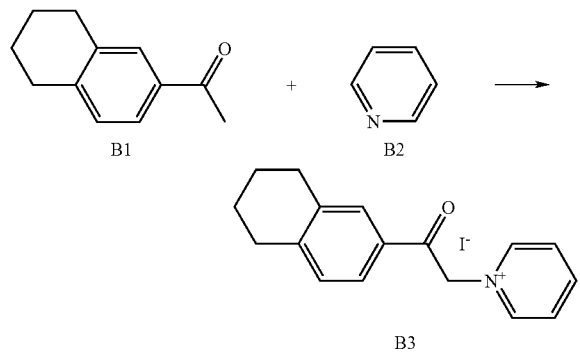

8.12 g (32 mmole) of Compound B1, 40 ml of pyridine (Compound B2), and 3.84 g (32 mmole) of iodine were fed into a 100-ml egg-plant type flask, and stirred at 110° C. for 6 hours in a stream of nitrogen. After filtering the reaction solution, the filtrate was washed with ethanol, and the precipitated crystal was filtered out to yield 19.0 g of crystals of Compound B3 which seemed to contain the pyridine solvent.

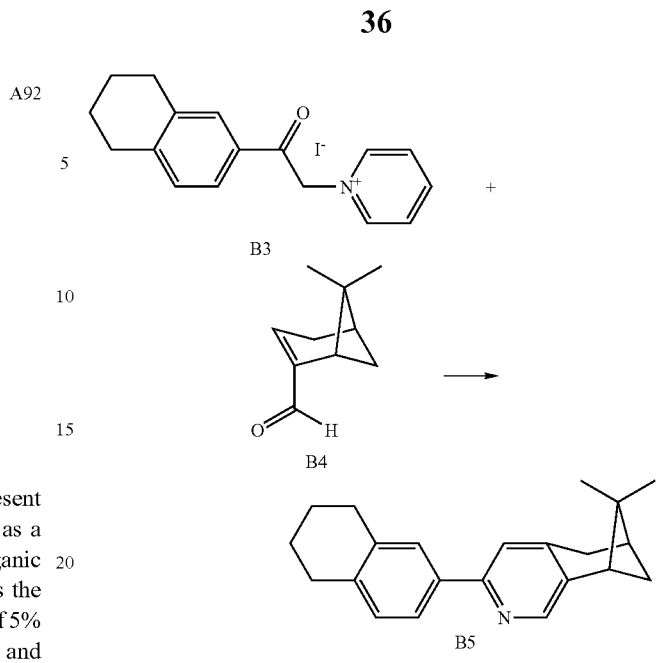

15.0 g of Compound B3, 3.8 g (25 mml) of Compound B4, 4.0 g (52 mmole) or ammonium acetate, and 40 ml of DMF were fed into a 100-ml three-necked flask, and stirred at 75° C. for 6 hours in a stream of nitrogen. The reaction product was cooled to room temperature. A precipitate was transferred to 80 ml of water, extracted five times with 300 ml of hexane for each time, and dried over magnesium sulfate, followed by filtration and concentration. After that, silica gel chromatography (toluene:hexane=1:1) was performed to fractionate a target product, and the target product was concentrated to yield 7.5 g of a white solid (Compound B5).

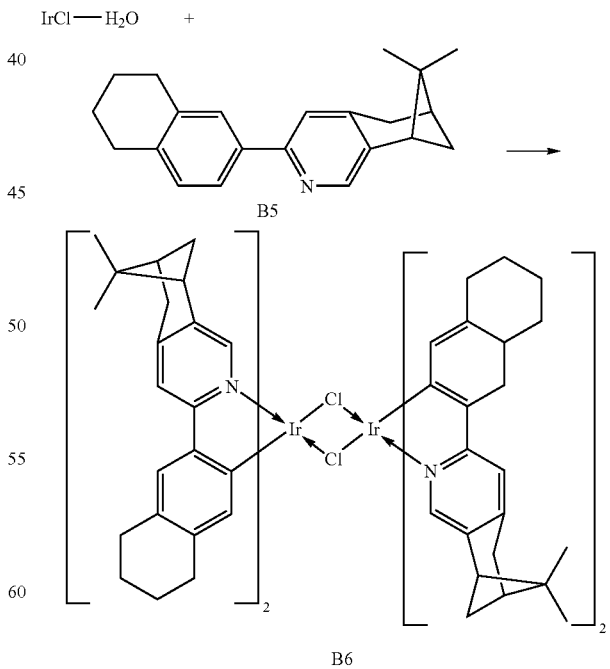

1.89 g (5 mmole) of an iridium (III) trihydrate, 3.67 g (11 mmole) of Compound B5, 90 ml of ethoxyethanol, and 30 ml of water were fed into a 200-ml three-necked flask, and stirred at room temperature for 30 minutes under a stream of nitrogen, followed by stirring at 100° C. for 10 hours. The reaction product was cooled to room temperature. A precipitate was filtrated out and washed with water and then with ethanol. The resultant product was dried under reduced pressure at room temperature to yield 3.8 g (75% yield) of a yellow powder of Compound B6.

chloroform/methanol to yield 1.2 g (72% yield) of a yellow powder of Exemplified Compound No. A60.

Example 2

Synthesis of Exemplified Compound No. A2

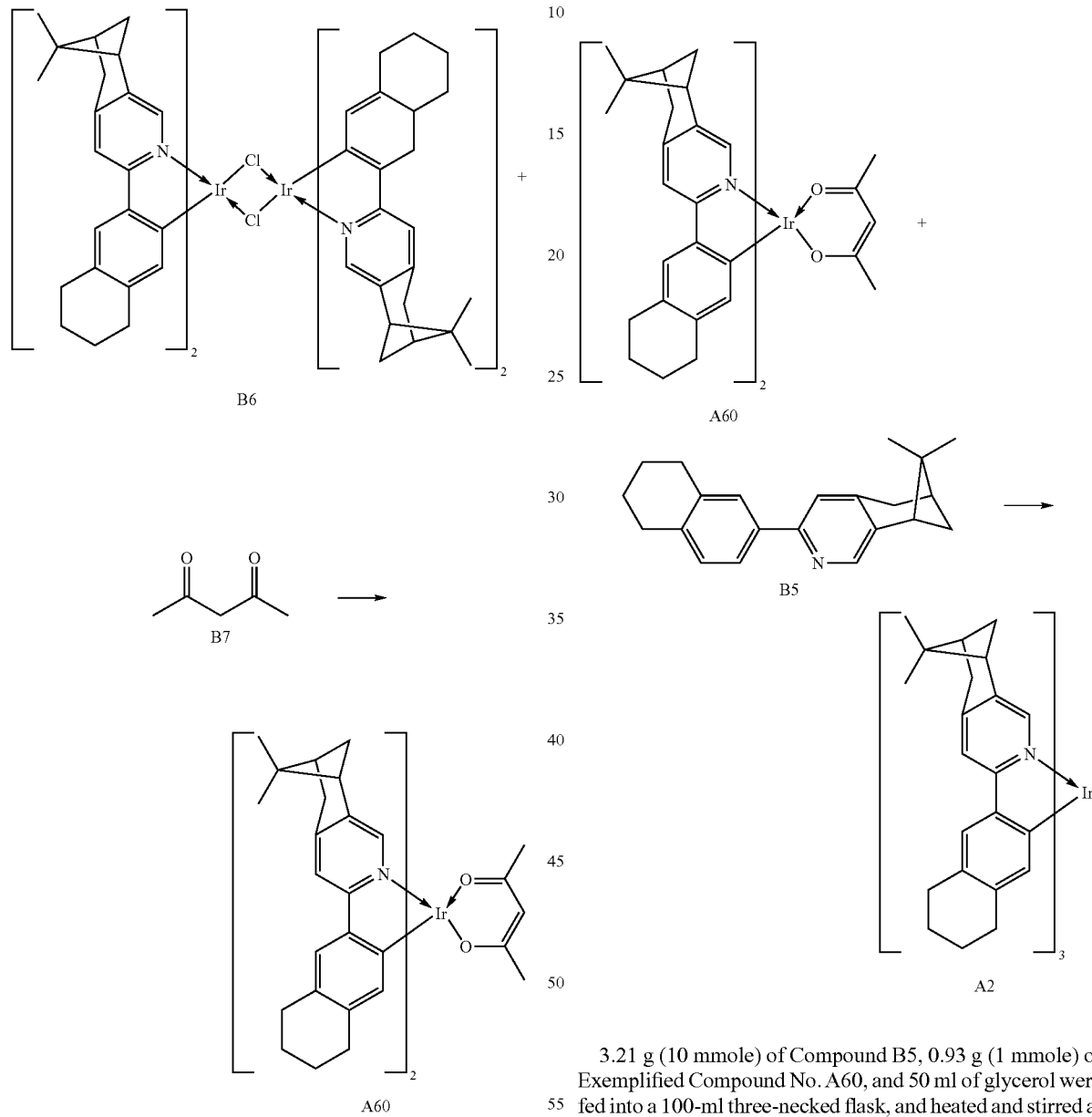

100 ml of ethoxyethanol, 1.67 g (1 mmole) of Compound B6, 0.2 g (2 mmole) of acetyl acetone (Compound B7), and 0.85 g (8 mmole) of sodium carbonate were fed into a 200-ml three-necked flask, and stirred at room temperature for 1 hour under a stream of nitrogen, followed by stirring at 100° C. for 7 hours. The reaction product was cooled with ice, and a precipitate was filtrated out and washed with water. The precipitate was washed with ethanol and dissolved in chloroform, followed by filtration of insoluble substances. The filtrate was concentrated and subjected to recrystallization with chloroform/methanol to yield 1.2 g (72% yield) of a yellow powder of Exemplified Compound No. A60.

3.21 g (10 mmole) of Compound B5, 0.93 g (1 mmole) of Exemplified Compound No. A60, and 50 ml of glycerol were fed into a 100-ml three-necked flask, and heated and stirred at around 180° C. for 8 hours under a stream of nitrogen. The reaction product was cooled to room temperature and poured into 170 ml of 1 N hydrochloric acid. A precipitate was filtrated out and washed with water, followed by drying under reduced pressure at 100° C. for 5 hours. The precipitate was purified by silica gel column chromatography using chloroform as an eluent to yield 0.15 g (13% yield) of a red powder of Exemplified Compound No. A2.

Exemplified Compound No. A2 was confirmed to have M+ of 1,099.54 according to MALDI-TOF MS and λmax=521 nm (in toluene).

Example 3
Synthesis of Exemplified Compound No. A37
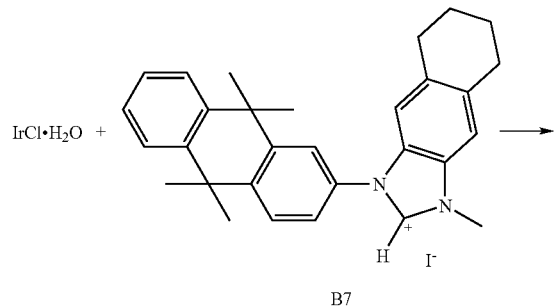
B7
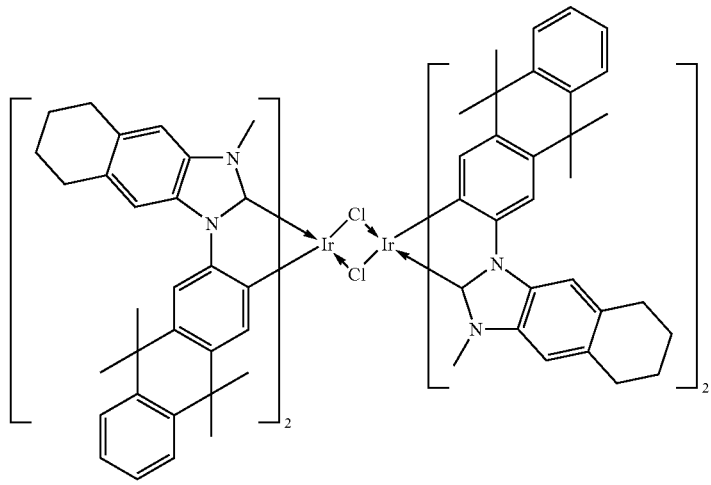
B8
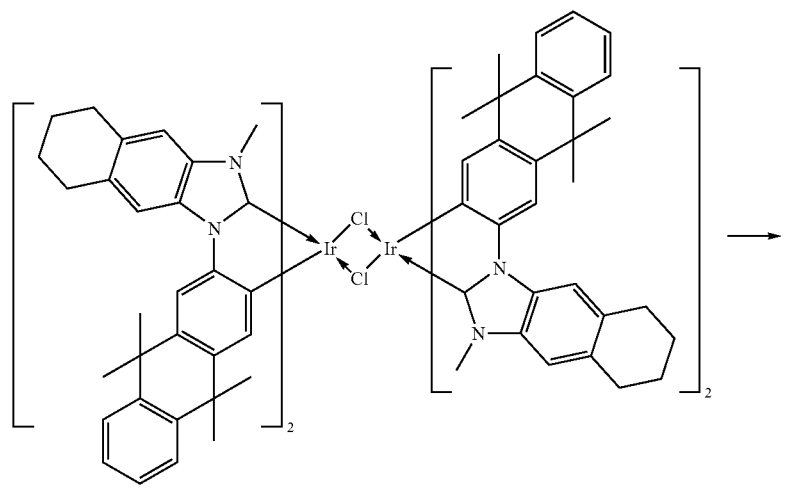
B8

-continued

A37

A reaction as described in the above-mentioned reaction formulae is carried out using iridium (III) trihydrate, Compound B7, silver (I) oxide, and dehydrated THF to yield Exemplified Compound No. A37.

Example 4

Figure 7:
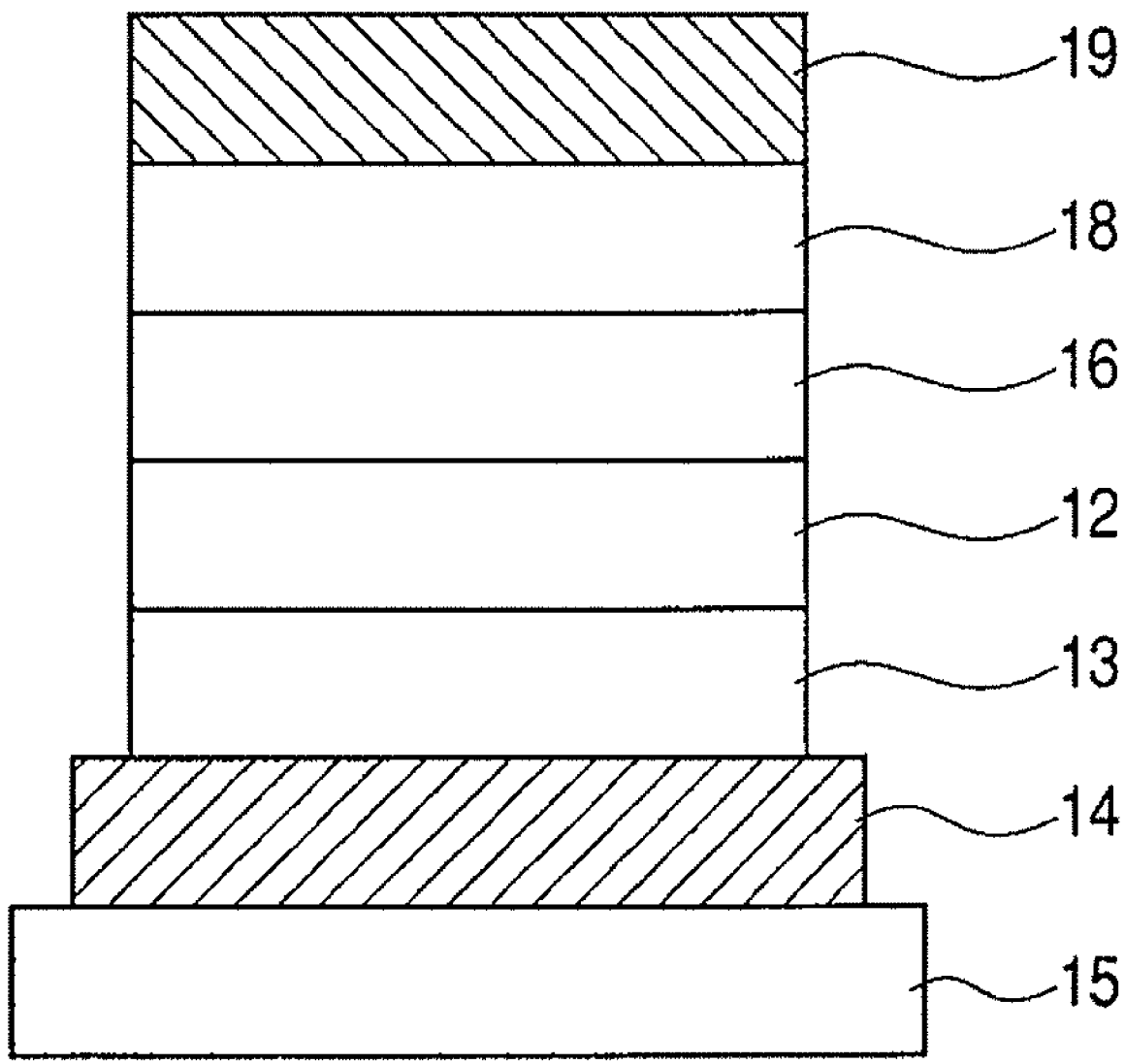
FIG. 7 shows another example of the organic EL device of the present invention.

In this example, a device having 3 organic layers shown in FIG. 7 was used as a device constitution. A pattern of ITO (transparent electrode 14) having a thickness of 100 nm was so formed on a glass substrate (transparent substrate 15) as to have an electrode area of 3.14 mm². The following organic layers and electrode layers were successively formed on the ITO substrate through vacuum evaporation according to resistance heating in a vacuum chamber at $10^{-4}$ Pa to produce a device. Hole-transporting layer 13 (40 nm): Compound A of the following formula Light-emitting layer 12 (5 nm): Exemplified Compound No. A2

Electron-transporting layer 16 (30 nm): Bphen of the following formula

Metal electrode layer 18 (15 nm): KF

Metal electrode layer 19 (100 nm): Al

An electric current was applied to the device, and light emission was confirmed.

Compound A:

Bphen:

Example 5

In the device constitution shown in Example 4, a device having the following constitution was produced.
Hole-transporting layer 13 (40 nm): Compound A1
Light-emitting layer 12 (40 nm): 30% by weight of CBP+ Exemplified Compound No. A2
Electron-transporting layer 16 (30 nm): Bphen
Metal electrode layer 18 (15 nm): KF
Metal electrode layer 19 (100 nm): Al
Electric current was applied to the device, and light emission was confirmed with an emission peak at 525 nm.

Example 6

In the device constitution shown in Example 4, a device having the following constitution was produced
Hole-transporting layer 13 (40 nm): Compound A1
Light-emitting layer 12 (10 nm): Exemplified Compound No. A65
Electron-transporting layer 16 (30 nm): Bphen
Metal electrode layer 18 (15 nm): KF
Metal electrode layer 19 (100 nm): Al
Electric current was applied to the device, and light emission was confirmed.

Example 7

In the device constitution shown in Example 4, a device having the following constitution was produced.
Hole-transporting layer 13 (40 nm): Compound A1
Light-emitting layer 12 (10 nm): Exemplified Compound No. A10
Electron-transporting layer 16 (30 nm): Bphen Metal electrode layer 18 (15 nm): KF
Metal electrode layer 19 (100 nm): Al Electric current was applied to the device, and light emission was confirmed.

Example 8

PEDOT (for use in organic EL) manufactured by Bayer AG was applied onto an ITO substrate to have a thickness of 40 nm by spin coating at 1,000 rpm for 20 seconds. The resultant layer was dried in a vacuum chamber at 120° C. for 1 hour. An organic film (light-emitting layer 12) was formed on the resultant film to have a thickness of 50 nm by spin coating under a nitrogen atmosphere at 2,000 rpm for 20 seconds using a solution containing the following components.
Dehydrated chlorobenzene: 10 g
Exemplified Compound No. A2: 92 mg
Compound B: 8 mg Compound B:

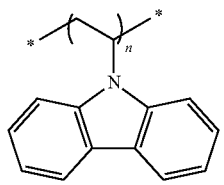

After the formation of the organic film, the organic film was dried under the same conditions as in the case of forming the PEDOT film.

The substrate thus produced was set in a vacuum evaporation chamber to form a film of Bphen in a thickness of 40 nm by vacuum evaporation deposition. The organic layers had a total film thickness of 130 nm.

Next, a cathode (metal electrode 11) having the following constitution was formed.
Metal electrode layer 1 (15 nm): an Al/Li alloy (Li content of 1.8% by weight)
Metal electrode layer 2 (100 nm): Al After the completion of film formation, the device was taken out for evaluation.

A DC voltage was applied to the device in such a manner that a minus voltage was applied to the metal electrode 11 and a plus voltage was applied to the transparent electrode 14 to evaluate the device properties. Electric current was applied to the device, and light emission was observed.

The organic compound of the present invention including a metal complex in which an alicyclic structure is directly bound to an aromatic ring structure present for each conformation can be used for a light-emitting material for a light-emitting device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-099893, filed Mar. 31, 2006, which is hereby incorporated by reference herein in its entirety.

What is claimed is:

1. A compound for a light-emitting device which is represented by the following general formula (7):

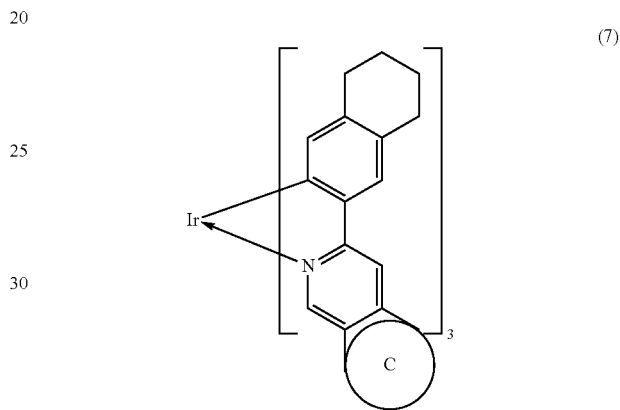

wherein C represents an alicyclic structure and the alicyclic structure may have a linear or branched alkyl group having 1 to 20 carbon atoms as a substituent.

2. A light-emitting device comprising a pair of electrodes and a light-emitting layer disposed between the pair of electrodes, wherein the light-emitting layer comprises the compound according to claim 1.

3. A display apparatus comprising the light-emitting device according to claim 2 and a drive portion connected to the light-emitting device.

* * * * *